United States Patent [19]

Turon-Lagot

[11] Patent Number: 4,781,469

[45] Date of Patent: Nov. 1, 1988

[54] DETECTING PROXIMITY OR OCCURRENCE OF CHANGE OF PHASE WITHIN A FLUID

[75] Inventor: Gilbert Turon-Lagot, Rueil Malmaison, France

[73] Assignee: Electricite de France, Paris, France

[21] Appl. No.: 802,209

[22] Filed: Nov. 25, 1985

[30] Foreign Application Priority Data

Nov. 23, 1984 [FR] France ................. 84 17907

[51] Int. Cl.$^4$ ........................................... G01N 25/08
[52] U.S. Cl. ........................................ 374/27; 376/247
[58] Field of Search ............... 374/11, 27, 164, 12, 374/163, 169, 16; 376/245

[56] References Cited

U.S. PATENT DOCUMENTS

| | | | |
|---|---|---|---|
| 3,392,570 | 7/1968 | Bonjour et al. | 374/11 |
| 3,487,201 | 12/1969 | Beranek | 374/169 X |
| 3,564,900 | 2/1971 | Andre et al. | 374/25 |
| 4,227,411 | 10/1980 | Abramovich | 374/21 X |
| 4,399,823 | 8/1983 | Donnelly | 374/163 X |
| 4,408,902 | 10/1983 | Peuker | 374/27 |
| 4,449,403 | 5/1984 | McQueen | 376/247 X |
| 4,541,730 | 9/1985 | Comey et al. | 374/164 X |

FOREIGN PATENT DOCUMENTS 2721232  2/1978  Fed. Rep. of Germany ........ 374/27

*Primary Examiner*—Daniel M. Yasich
*Attorney, Agent, or Firm*—Larson and Taylor

[57] ABSTRACT

For detecting the occurrence or the imminence of a change of phase within a fluid, a predetermined quantity of heat is generated within thermally conducting means in contact with the fluid. The temperature of said means is measured and compared with a reference temperature so selected as to correspond to the apparition of a second phase within said fluid. In particular, effective or imminent apparition of gas bubbles can be detected in a liquid wherein the temperature of the thermally conducting means has a reference temperature close to the temperature of the liquid.

9 Claims, 1 Drawing Sheet

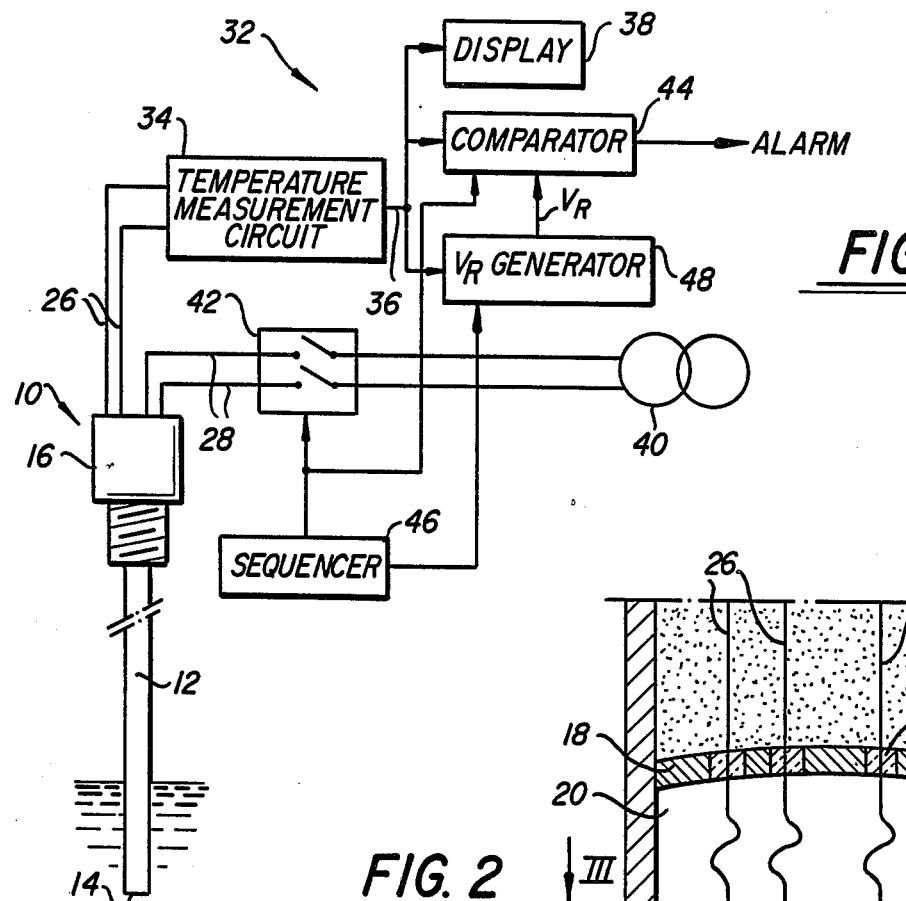
FIG. 1
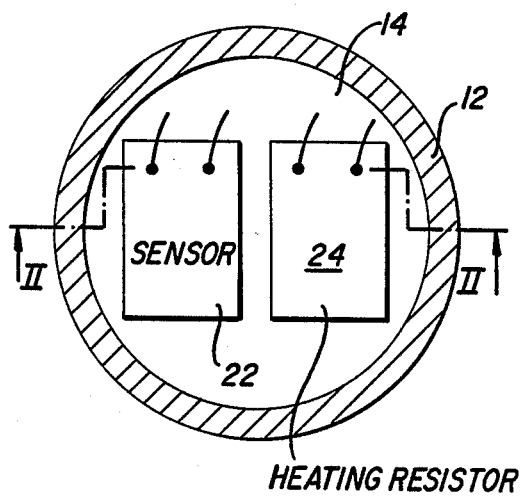
FIG. 2
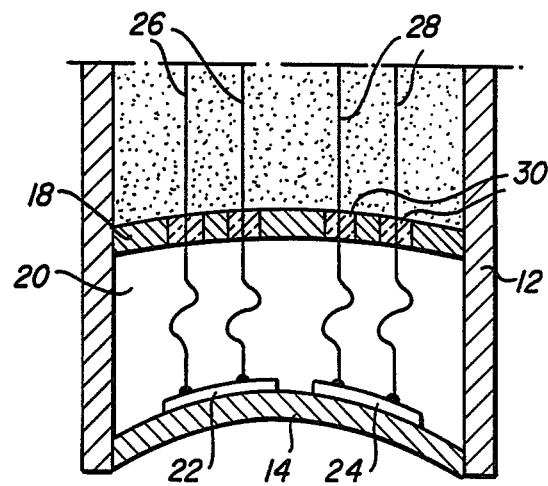
FIG. 3
FIG. 4

DETECTING PROXIMITY OR OCCURRENCE OF CHANGE OF PHASE WITHIN A FLUID

BACKGROUND OF THE INVENTION

1. FIELD OF THE INVENTION

The invention concerns detection of the proximity of change of phase within a fluid.

This invention should be especially useful when it is necessary to detect the apparition or the imminence of local boiling phenomenon within a liquid or more generally the presence of bubbles within the liquid.

Among the fields in which the invention is particularly suitable for use, there is the field of nuclear Pressurized Water Reactors, where temperature and pressure conditions generating a local boiling of the coolant of the reactor have to be avoided, since damage to the nuclear fuel assemblies could happen.

2. STATE OF THE ART

Various methods have existed for a long time for determining the occurrence of a phase change. For instance, there is disclosed in European Pat. No. 056 454 a method for finding the boiling point of a brake oil. The method includes delivering electrical current to a sensor for heating it until a temperature variation curve shows a change revealing boiling.

This has drawbacks, for instance, it does not allow detection of the imminence of boiling, the object of the invention being to find the boiling point by increasing the voltage until obtaining the change of phases. In a general way, none of the previous methods teaches or suggests monitoring of change of phase in a way which could prevent, particularly in the case of nuclear reaction, operational problems and safety hazards.

SUMMARY OF THE INVENTION

It is an object of the invention to provide an improved method and device for detecting proximity of change of phase within a fluid. It is a more specific object to achieve monitoring and safety of operations involving such fluid, within, among others, pressurized water reactors (PWR).

To this end there is provided a method including the steps of generating a predetermined heat quantity by the Joule effect within thermally conducting means in contact with the fluid measuring the temperature of said means, and comparing with a reference temperature so selected as to correspond to the apparition of a second phase within the fluid.

The detection is based on the fact that the heat conductivity of a fluid initially in a homogeneous liquid phase, is considerably diminished when gas bubbles appear. When it is intended to detect the imminence of the apparition of the vapor phase, a local boiling is generated by a rise of the temperature of the fluid due to heat dissipated by the Joule effect.

In any case, there is a diminution of heat conductivity which, in turn, abruptly raises the temperature of the thermally conducting means, giving a better reliability to the measurement.

The heat quantity generated can be dissipated within heating means such as electrical resistance, placed inside of a metallic sensor, against a face of said sensor in contact with the fluid.

The measurement can be made, either with a separated sensor such as an electrical resistor, a thermistor or a thermocouple, or by measuring the resistance of the heating means themselves when this resistance changes notably and has a well known relationship with the temperature. When the latter solution is retained, the heating means can be energized with a DC current, which, even of low value can generate a consequent rise of temperature, which will be very different according to whether vapor bubbles are present or not in the fluid normally in an homogeneous liquid phase.

The invention also provides a device for implementing the above defined method.

This device for detecting the proximity of a change of phase within a fluid comprises a sensor which can be placed in the fluid and which has a thermally conducting face in contact with an electrical resistor connected to electrical conducting means allowing energizing of said resistance with a predetermined heating current, and measurement means for monitoring the temperature of said conducting face which can be concave to trap gas bubbles.

The measurement means may incorporate the heating resistor or include a separate sensor.

The device will typically include an electric or electronic box which can be far away from the sensor and connected with the resistor and the sensor by isolated electric wires.

This box may be of various types; very simple if the boiling temperature of the fluid is well known; with means for modifying a temperature threshold in other cases, particularly when the boiling temperature changes notably with pressure changes.

The device is preferably operated for realizing in alternance several different measures, for example in repeating a predetermined cycle, such as measurement of the temperature of the liquid while the electrical resistor is not power supplied, and then detection of the apparition of a second phase or of the approach of conditions of such apparition.

BRIEF DESCRIPTION OF THE DRAWINGS

The invention will be better understood from reading the following description of a particular embodiment, given by way of non-limitative examples. The description refers to the accompanying drawings in which:

FIG. 1 is a general diagram of a device constituting a particular embodiment of the invention.

FIG. 2 is a sectional side elevational view of a portion of an embodiment of the invention showing shows a possible constitution of the end part of the sensor appearing in the device of FIG. 1, and in section through II—II of FIG. 3.

FIG. 3 is a section through III—III of FIG. 2.

FIG. 4 is a sectional side elevational view of a portion of an embodiment of the invention showing a further possible construction in which the end part of the sensor is concave.

DETAILED DESCRIPTION OF THE INVENTION

Referring to FIG. 1, there is schematically shown a device which includes a sensor 10 to be placed in a liquid in order to detect the effective or imminent apparition of vapor in the zone into which the end part of the sensor has been plunged.

The latter includes a tubular main part 12 closed by a bottom 14 and connected to an output tight connector 16.

A partition 18 delimits with the bottom 14 a chamber 20.

The wall of mainpart 12 situated above the partition 18 contains a thermal and electrical insulating, generally mineral compatible with the operating temperature.

On the bottom 14 are fixed, one beside the other, a thermal sensor 22 and a heating resistor 24. They may have the same construction, in which case they are constituted by an electrical resistor having a band shape, for example in platinum in the case of an application for detecting boiling within a pressurized water reactor or PWR. To each band are connected two or three electrical conductors 26 or 28 which go through the partition 18 through isolating tight cable glands 30 and are able to be connected with the connector 16 to an electronic box 32.

In the case of the particular realization shown on FIG. 1, box 32 is designed to allow determination of the temperature of the fluid in which sensor 10 is plunged.

For this purpose the conductors 26 are connected to a temperature measuring circuit 34 giving, in its output 36, an electrical output signal having an amplitude representative of the temperature of the sensor 22. The sensor 22 could have a resistance which varies with the temperature; in this case the circuit 34 will generally be a Wheatstone bridge. It could also be a thermocouple. Circuit 34 then delivers an amplified signal representative of the value of the voltage across the cold and the hot junctions.

When the heating resistor 24 is not power supplied, the output signal given by circuit 34 is representative of the temperature of partition 14 and therefore of the fluid. It then will be possible to display or record this signal on output equipment 38.

Box 32 further includes means for generating a heating current of a predetermined value within the heating resistor 24. On FIG. 1, the heating resistor 24 is power supplied by a steady current generator 40 through a contact switch 42 allowing measurement of the fluid temperature when the switch is open and detection of the apparition of a change of phase when the switch is closed.

In the second case, the output signal of the measurement circuit 34 is generated within a threshold circuit 44 giving an output signal which gives an indication when the voltage exceeds a reference voltage $V_R$ appropriately chosen or when it exceeds the reference voltage by a predetermined value.

The voltage is $V_R$ preferably adjustable and set corresponding to a temperature just below the boiling point of the liquid in which the sensor is immersed, when the boiling point is well known, which means that all the conditions interfering with it are steady. The detection is therefore performed with a good reliability, because start up of boiling which induces the apparition of bubbles will cause a considerable increase in the temperature of the sensor 22. That temperature will go from a value close to the temperature of the fluid, to a much higher temperature because of the diminution of the thermal conductivity.

On the other hand, when the boiling point may vary within large limits, for example when there are changes of pressure of the liquid, it could be better to add to box 32 means of automatic regulation of the reference value of the voltage $V_R$. In the case shown in FIG. 1, these means include a sequencer 46 which opens and closes alternatively contact switch 42 and enables in alternance, either a comparator 44, or a generator 48 of the reference voltage $V_R$.

When circuit 48 is enabled, it delivers a voltage $V_R$, then forwarded to comparator 44, such tension being representative of the real fluid temperature, detected by circuit 34 when contact switch 42 is open.

The operation of the device is as follows:

In a first step, the sequencer 46 opens contact switch 42 and actuates the generator 48. The latter generates and stores a voltage $V_R$ representative of the temperature of the thermal sensor 22.

In the second step, sequenser 46 closes the contact switch and actuates the comparator 44. When the difference between the output given by circuit 34 and reference voltage $V_R$ go over a predetermined value which can be fixed or adjustable, an alarm output signal is emitted.

When it is not the presence of vapor, but the imminence of the constitution of vapor which is monitored, a greater value of the heating current is chosen, therefore causing a local boiling when the difference between the actual temperature and the boiling point is less than a value selectable in advance.

In a further embodiment of the invention, a single element constitutes the heating device 24 and the sensor 22. This single element may be a flat metallic resistor. In this case sequencer 46 is preferably designed to deliver a heating pulse, for determining the temperature of the element after the pulse. An other solution consists in supplying permanently the single element with a steady current, therefore causing a substantial heating and in determining the temperature of the element which will be much higher in the presence of gas bubbles than in a homogeneous liquid.

When sensor 22 is distinct from the heating device 24, it may be of very diverse nature such as an electric resistor, a thermistor or a thermocouple.

What is claimed is:

1. A method for detecting imminency of boiling in liquid body, comprising the steps of:
    (a) delivering a predetermined quantity of heat by resistance electric heating, with an electrical resistor, to a portion of a thermally conducting means which is in contact with the liquid body for bringing said thermally conducting means to an increased temperature at said portion,
    (b) sensing said increased temperature and providing, ressponsive thereto, an increased temperature signal representative of said increased temperature,
    (c) comparing said increased temperature signal with a reference temperature signal having a value such that local boiling of said liquid body is indicated by a difference between said increased temperature signal and said reference temperature signal, and
    (d) repeating steps a, b, and c.

2. The method according to claim 1, for detecting imminence of boiling in a liquid body, wherein the increased temperature signal is compared with a reference temperature signal representative of a temperature which is close to the temperature of said liquid body.

3. The method according to claim 1, wherein the predetermined quantity of heat is generated by a predetermined electric current supplied within an electrical resistor which is in contact with said thermally conducting means.

4. The method according to claim 3 wherein a d.c. current is supplied to said resistor, the value of said resistor is measured; and the temperature of said resistor and therefore said thermally conducting means is deduced from the measured value.

5. The method according to claim 3 wherein producing of said increased temperature signal is effected with signal producing means distinct from the electrical resistor.

6. The method according to claim 5, wherein said signal producing means comprises the electrical resistor, a thermistor or a thermocouple.

7. The method according to claim 5 wherein
in step (a), said electrical resistor is alternately energized and deenergized,
in step (b), with said signal generation means said reference temperature signal is produced when the electrical resistor is deenergized and the increased temperature signal is produced when said electrical resistor is energized, and
in step (c), the results of said signals are compared.

8. A device for detecting imminence of boiling a liguid body comprising:
   (a) a sensor for location in the liquid body and which has a thermally conducting face having a temperature,
   (b) first conducting means connected to said sensor for delivering signals representing the value of the temperature of the thermally conducting face of said sensor to measurement means;
   (c) measurement means comprising a temperature measuring circuit, a generator of reference voltage representative of a reference voltage representative of a reference temperature, and a comparator circuit for comparison of the temperature of said said sensor with said reference temperature,
   (d) an electrical heating resistor in contact with the thermally conducting face of said sensor,
   (e) second conducting means connected to said resistor for circulating a predetermined electrical current in said resistor for heating said resistor,
   (f) means for generating said predetermined electrical current, and
   (g) a sequencer for enabling, alternatively either the comparator circuit or reference voltage generator.

9. The device according to claim 8, wherein said thermally conducting face is concave and turned downwardly whereby said concave face traps gas bubbles generated within the boiling liquid body.

* * * * *